(12) United States Patent
Boyd et al.

(10) Patent No.: US 8,506,196 B2
(45) Date of Patent: Aug. 13, 2013

(54) FLUID DELIVERY SYSTEM FOR AN ORAL CARE IMPLEMENT

(75) Inventors: Thomas Boyd, Metuchen, NJ (US); Sharon Kennedy, Randallstown, MD (US); Madhusudan Patel, Somerset, NJ (US); John Gatzemeyer, Hillsborough, NJ (US); Eduardo Jimenez, Manalapan, NJ (US)

(73) Assignee: Colgate-Palmolive Company, New York, NY (US)

( * ) Notice: Subject to any disclaimer, the term of this patent is extended or adjusted under 35 U.S.C. 154(b) by 700 days.

(21) Appl. No.: 12/713,908

(22) Filed: Feb. 26, 2010

(65) Prior Publication Data

US 2011/0211901 A1    Sep. 1, 2011

(51) Int. Cl.
  *B43K 8/06*  (2006.01)
  *B43K 8/08*  (2006.01)

(52) U.S. Cl.
  USPC ............ 401/198; 401/199; 401/205; 222/187

(58) Field of Classification Search
  USPC ..................... 401/198, 199, 205; 222/187
  See application file for complete search history.

(56) References Cited

U.S. PATENT DOCUMENTS

| | | |
|---|---|---|
| 1,798,081 A | 3/1931 | Gordyn, Jr. et al. |
| 1,973,212 A | 9/1934 | Krueger |
| 2,573,201 A | 10/1951 | Kelley et al. |
| 2,594,721 A | 4/1952 | Beebe |
| 2,739,328 A | 3/1956 | Bernier |
| 3,369,543 A | 2/1968 | Ronco |
| 3,685,080 A | 8/1972 | Hubner |
| 3,810,479 A | 5/1974 | Miles |
| 3,903,888 A * | 9/1975 | Buelow et al. ................ 604/186 |
| 3,910,706 A | 10/1975 | Del Bon |
| 3,936,200 A | 2/1976 | O'Rourke |
| 3,937,582 A | 2/1976 | Del Bon |

(Continued)

FOREIGN PATENT DOCUMENTS

| | | |
|---|---|---|
| CN | 2343878 Y | 10/1999 |
| DE | 3832520 | 4/1990 |

(Continued)

OTHER PUBLICATIONS

International Search Report and Written Opinion of corresponding International Application No. PCT/US2010/025605 dated Nov. 19, 2010.

(Continued)

*Primary Examiner* — David Walczak
*Assistant Examiner* — Joshua Wiljanen
(74) *Attorney, Agent, or Firm* — Ryan M. Flandro

(57) ABSTRACT

A fluid delivery system usable in an oral care implement and a reservoir containing a flowable substance. A capillary channel formed of one or more wicking or capillary members extends through at least a portion of the oral care implement to deliver flowable substance(s) through one or more outlets via capillary action. In one embodiment, the rate of fluid flow through the capillary channel is different in at least a first flow section than in a second flow section. In another embodiment, the rate of flow between flow sections of the wicking member is different than in at least one of the flow sections. A variety of flowable substances can be administered for therapeutic, hygienic, and/or other benefits, such as fresh breath, tooth whitening, tooth sensitivity, plaque and/or tartar control, or producing sensations of heat, cool, or tingling.

19 Claims, 10 Drawing Sheets

(56) References Cited

U.S. PATENT DOCUMENTS

| | | |
|---|---|---|
| 4,023,580 A | 5/1977 | Pieters |
| 4,088,412 A | 5/1978 | Del Bon |
| 4,124,316 A | 11/1978 | O'Rourke |
| 4,236,651 A | 12/1980 | Meyer et al. |
| 4,543,679 A | 10/1985 | Rosofsky et al. |
| 4,585,018 A | 4/1986 | O'Connor |
| 4,733,586 A | 3/1988 | Manusch et al. |
| 5,017,036 A | 5/1991 | Vidovic |
| 5,062,728 A | 11/1991 | Kuo |
| 5,066,155 A | 11/1991 | English et al. |
| 5,088,627 A | 2/1992 | Musel |
| 5,096,319 A | 3/1992 | Gueret |
| 5,098,297 A | 3/1992 | Chari et al. |
| 5,102,251 A | 4/1992 | Kaufmann |
| D337,659 S | 7/1993 | Lacy |
| 5,309,590 A | 5/1994 | Giuliani et al. |
| 5,346,324 A | 9/1994 | Kuo |
| 5,352,052 A | 10/1994 | Kaufmann |
| 5,476,384 A | 12/1995 | Giuliani et al. |
| 5,490,736 A | 2/1996 | Haber et al. |
| 5,611,687 A | 3/1997 | Wagner |
| 5,769,553 A | 6/1998 | Chaudhri et al. |
| 5,865,195 A | 2/1999 | Carter |
| 6,039,489 A | 3/2000 | Harman et al. |
| 6,089,776 A | 7/2000 | Kaufmann |
| 6,095,707 A | 8/2000 | Kaufmann |
| 6,142,694 A | 11/2000 | Rivlin et al. |
| 6,164,858 A | 12/2000 | Kaufmann |
| 6,183,155 B1 | 2/2001 | Kaufmann |
| 6,203,320 B1 | 3/2001 | Williams et al. |
| 6,205,611 B1 | 3/2001 | Vigil |
| 6,206,600 B1 | 3/2001 | Rosenberg et al. |
| 6,244,774 B1 | 6/2001 | Barosso et al. |
| 6,322,268 B1 | 11/2001 | Kaufmann et al. |
| 6,371,674 B1 | 4/2002 | Lerner |
| 6,434,773 B1 | 8/2002 | Kuo |
| D465,625 S | 11/2002 | Price |
| 6,497,527 B2 | 12/2002 | Kaufmann |
| RE38,150 E | 6/2003 | Greatbach et al. |
| 6,669,930 B1 | 12/2003 | Hoic et al. |
| 6,770,266 B2 | 8/2004 | Santarpia, III et al. |
| 6,802,097 B2 | 10/2004 | Hafliger et al. |
| 6,817,803 B1 | 11/2004 | Ong et al. |
| 6,899,280 B2 | 5/2005 | Kotary et al. |
| D510,482 S | 10/2005 | Jimenez |
| 7,003,839 B2 | 2/2006 | Hafliger et al. |
| 7,025,521 B2 | 4/2006 | Tsaur |
| 7,143,462 B2 | 12/2006 | Hohlbein |
| 7,201,527 B2 | 4/2007 | Thorpe et al. |
| 7,281,670 B2 | 10/2007 | Lakatos et al. |
| 7,303,143 B2 | 12/2007 | Davis et al. |
| 7,311,456 B1 | 12/2007 | Neal |
| 7,322,067 B2 | 1/2008 | Hohlbein |
| 7,478,960 B2 | 1/2009 | Glover |
| 7,596,974 B2 | 10/2009 | Smith et al. |
| 2003/0086743 A1 | 5/2003 | Gruenbacher et al. |
| 2004/0020508 A1 | 2/2004 | Earl |
| 2004/0182414 A1 | 9/2004 | Puskas |
| 2004/0237226 A1 | 12/2004 | Hohlbein et al. |
| 2004/0255416 A1 | 12/2004 | Hohlbein |
| 2005/0091769 A1 | 5/2005 | Jimenez et al. |
| 2005/0147461 A1 | 7/2005 | Glover |
| 2005/0201812 A1 | 9/2005 | Wong et al. |
| 2005/0217688 A1 | 10/2005 | Liu et al. |
| 2005/0218033 A1 | 10/2005 | Curtis |
| 2005/0220530 A1 | 10/2005 | Carmona |
| 2005/0232687 A1 | 10/2005 | Zeh et al. |
| 2005/0233279 A1 | 10/2005 | Zeh et al. |
| 2006/0228163 A1 | 10/2006 | McSweeny |
| 2006/0280548 A1 | 12/2006 | Sharpe |
| 2007/0020032 A1 | 1/2007 | Abbas |
| 2007/0101525 A1 | 5/2007 | Hohlbein |
| 2007/0183838 A1 | 8/2007 | Umar |
| 2007/0223988 A1 | 9/2007 | Gruenbacher et al. |
| 2008/0014010 A1 | 1/2008 | Bartschi et al. |
| 2008/0044791 A1 | 2/2008 | Tsurukawa et al. |
| 2008/0176183 A1 | 7/2008 | Gatzemeyer et al. |
| 2009/0052972 A1 | 2/2009 | DellaCorte |
| 2009/0060622 A1 | 3/2009 | Lian et al. |
| 2009/0180826 A1 | 7/2009 | Guay |
| 2009/0258326 A1 | 10/2009 | Al-Sulaiman et al. |
| 2009/0261179 A1 | 10/2009 | Hall |
| 2009/0320226 A1 | 12/2009 | Robinson et al. |

FOREIGN PATENT DOCUMENTS

| | | |
|---|---|---|
| DE | 4139141 | 6/1993 |
| DE | 10035214 | 2/2002 |
| DE | 202004008909 U1 | 9/2004 |
| EP | 0092359 | 10/1983 |
| EP | 1639913 | 3/2006 |
| GB | 2205280 | 12/1988 |
| GB | 2394653 | 5/2004 |
| GB | 2430146 | 3/2007 |
| JP | 1-097406 | 4/1989 |
| JP | 2-43099 | 2/1990 |
| JP | 2-152405 | 6/1990 |
| JP | 2-297498 | 12/1990 |
| JP | 9-215524 | 8/1997 |
| JP | 2003-019023 | 1/2003 |
| KR | 20-0183429 | 5/2000 |
| NL | 9400631 | 12/1995 |
| RU | 2105519 | 2/1998 |
| WO | WO 92/10146 | 6/1992 |
| WO | WO 99/05987 | 2/1999 |
| WO | WO 03/000506 | 1/2003 |
| WO | WO 2006/019289 | 2/2006 |
| WO | WO 2006/032367 | 3/2006 |
| WO | WO 2007/073917 | 7/2007 |
| WO | WO 2011/106017 | 9/2011 |

OTHER PUBLICATIONS

International Search Report and Written Opinion of International Application No. PCT/US2008/051778 dated Dec. 12, 2008.
International Search Report and Written Opinion in International Application No. PCT/US11/027042, mailed Nov. 28, 2011.
PCT/US2008/051778—filed Jan. 23, 2008 International Search Report dated Aug. 4, 2008.

* cited by examiner

FLUID DELIVERY SYSTEM FOR AN ORAL CARE IMPLEMENT

FIELD

The present invention is directed to an oral care implement including a capillary delivery system for a flowable substance, such as an oral care fluid.

BACKGROUND

Oral care implements, particularly toothbrushes, are typically used by applying toothpaste to a bristle section followed by brushing regions of the oral cavity, e.g., the teeth, tongue, and/or gums. Some toothbrushes have been equipped with fluid reservoirs and systems for delivering oral care agents, such as whitening agents, breath freshening agents, and the like. There is a continuing need for alternative oral care implements for delivering auxiliary oral care fluids.

BRIEF SUMMARY

The present invention pertains to an oral care implement having a capillary delivery system. Optionally, the oral care implement has a head containing tooth cleaning elements on a first surface thereof.

In one embodiment, an oral care implement includes a reservoir containing at least one flowable substance. A variety of flowable substances can be administered for therapeutic, hygienic, and/or other oral care benefits, such as fresh breath, tooth whitening, or producing sensations of heat, cool, or tingling.

In another embodiment, an oral care implement includes a capillary channel extending through at least a portion of the implement to deliver the flowable substance to one or more outlets. In one embodiment, an outlet is located on a second surface of the head generally opposite the first surface that contains the tooth cleaning elements.

In yet another embodiment, an oral care implement has a head containing tooth cleaning elements, a reservoir for storing a flowable substance, and an overflow chamber. The reservoir and overflow chamber may be separated by a partition. A capillary channel constructed from a fibrous material, ceramic, porous plastic, or combination thereof extends through at least a portion of the implement to deliver the flowable substance to one or more outlets.

In another embodiment, an oral care implement has a head containing tooth cleaning elements, a reservoir containing at least one flowable substance, a capillary channel extending through at least a portion of the implement to deliver the flowable substance to one or more outlets, and a motion-producing device. When activated, the motion-producing device vibrates the implement or a portion thereof, such as the head portion. The vibration enhances the function of the tooth cleaning elements and also promotes delivery of the flowable substance through the capillary channel, which together provides an enhanced cleaning action.

According to another aspect of the invention, an oral care implement is provided including a handle for grasping, a head including at least one tooth cleaning element, a reservoir for storing a flowable substance, at least one outlet disposed on the head, and a capillary channel fluidly coupling the reservoir to the outlet. In some embodiments, the capillary channel further includes a first wicking member formed of a wicking material and defining a first flow section, a second wicking member formed of a wicking material and defining a second flow section. The second wicking member is fluidly coupled to the first wicking member and the flowable substance flows via capillary action through the first wicking member at a flow rate that is different than in the second wicking member. In some embodiments, the first and second wicking members are made of different materials having different capillarities.

According to another aspect of the invention, an oral care implement is provided that includes a handle for grasping, a head including at least one tooth cleaning element, a reservoir for storing a flowable substance, at least one outlet disposed on the head, and a capillary channel fluidly coupling the reservoir to the outlet. The capillary channel further includes a first wicking member formed of a wicking material and defining a first flow section, a second wicking member formed of a wicking material and defining a second flow section. The second wicking member is fluidly coupled to the first wicking member and the flowable substance flows via capillary action from the first wicking member to the second wicking members through a flow restrictor at a reduced rate of flow that is smaller than a rate of flow through the first or second wicking members. In one embodiment, the flow restrictor is a reduced cross-sectional flow area disposed between the first and second wicking members that is operative to reduce the flow therebetween. In some embodiments, the flow restrictor may be a notched area formed between the first and second wicking members. The first and second wicking members may be a unitary member or separate members fluid coupled together.

BRIEF DESCRIPTION OF THE DRAWINGS

The features and advantages of the invention will be apparent from the following more detailed description of certain embodiments of the invention and as illustrated in the accompanying drawings in which.

DETAILED DESCRIPTION

Figure 1:
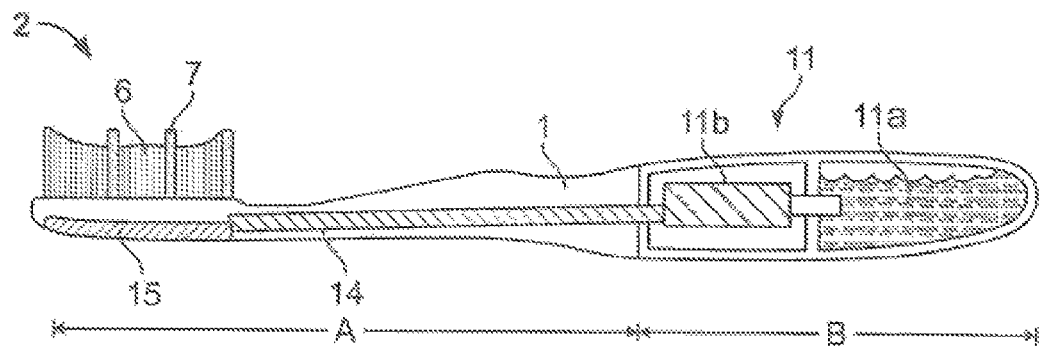
FIG. 1 is a schematic illustration of a toothbrush according to one embodiment of the invention.

FIG. 1 schematically illustrates a toothbrush having a handle 1 and a head 2 containing one or more tooth cleaning elements, such as bristles 6 and/or elastomeric cleaning elements 7. A reservoir 11 is provided for storing a flowable substance. The flowable substance is most often a fluid in the form of a liquid, but can be in other forms, e.g., semi-solid, paste, or gel. The reservoir 11 can include a liquid storage tank 11a in fluid communication with a delivery section 11b. A capillary channel 14 generally extends in the longitudinal direction of the toothbrush for delivering the flowable substance from the reservoir 11 to at least one outlet 15.

In one aspect, the outlet 15 can be located on a surface of the head 2 generally opposite the surface that contains the tooth cleaning elements 6 and 7. In another aspect, the outlet 15 can be located within the bristles 6 and/or elastomeric cleaning elements 7. Optionally, a plurality of outlets may be provided on both the surface of the head that contains the tooth cleaning elements as well as the opposite the surface of the head, e.g., for delivering the same flowable substance from a common supply or different flowable substances from separate supplies.

The channel 14 uses capillary action to draw flowable substance from the reservoir 11 to the outlet 15. The outlet 15 can be configured as a non-woven pad, membrane or other structure that allows passage of the medium containing the flowable substance. Examples of materials that can be used for the outlet include porous plastics and other porous materials, such as those described below with reference to the capillary channel 14.

The capillary channel 14 generally has a capillary structure and usually is a porous material. Examples of suitable materials include fibrous materials, ceramics, and porous plastics such as those available from Porex Technologies, Atlanta, Ga. One example of a fibrous material is an acrylic material identified as type number C10010, available from Teibow Hanbai Co., Ltd., Tokyo, Japan. A mixture of porous and/or fibrous materials may be provided which have a distribution of larger and smaller capillaries. The channel can be formed from a number of small capillaries that are connected to one another, or as a larger single capillary tube.

The reservoir 11 may be formed from any suitable material and may include reticulated foam, which may range from hydrophilic to hydrophobic. Hydrophobic foams may be used with non-water based liquids. An example of a reticulated foam is Bulpren S90, manufactured by Recticel (Wetteren, Belgium). Bulpren S90 is an open cell polyurethane foam based on polyester which averages 90 pores per inch. Other examples of materials that can be used for the reservoir 11 include ceramics and porous plastics. In a preferred embodiment, the reservoir may be a commercially available bonded fiber component from Filtrona or Porex, such as without limitation polypropylene, polyethylene, or copolymers of such polymers in varying ranges of hydrophobicity depending on the composition selected.

Non-limiting examples of capillary configurations that can be used are shown in FIGS. 4-7. The capillary devices 10 generally have a housing 20 that includes a reservoir 11 for storing fluid 13 and an overflow chamber 25. The reservoir 11 and overflow chamber 25 may be separated by a partition 21, for example, or otherwise separated such as described below with reference to FIG. 7. The reservoir 11 may be an integral part of housing 20 or a separate element connected to the housing. An inlet 22 allows air to flow freely into and out of overflow chamber 25.

Partition 21 may include an opening 12 which is closed by the capillary channel 14. The channel 14 generally extends from the opening 12 to the outlet 15 and is in direct contact with a capillary storage 16. The average capillarity of the capillary storage 16 is generally smaller than the average capillarity of channel 14. Although the capillary storage is arranged about the periphery of capillary channel 14, it does not necessarily extend all the way around the channel. Strict separation of capillary storage 16 and channel 14 is not necessary.

The capillary channel 14 can be press-fit into an opening in the handle 1 or, alternatively, the handle 1 can be overmolded around the capillary channel 14. In a preferred method of manufacturing, channel 14 is formed separately and inserted into handle 1. The capillary channel 14 generally provides the only path by which air can enter the otherwise closed reservoir 11. The finer capillaries of channel 14 transfer flowable substance to the outlet 15. The larger capillaries allow air to enter the reservoir 11. In general, air can enter through at least the largest capillary in the channel.

Figure 5:
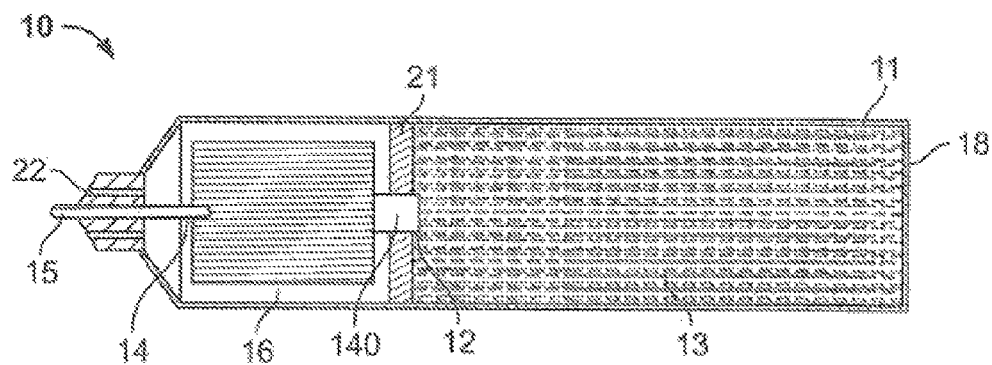

With reference to FIG. 5, by way of example, when air expansion takes place within the reservoir 11, a portion of the flowable substance 13 in the reservoir 11 will be transferred through an opening 12 and channel 14 into the normally flowable substance-free portions of capillary storage 16. In other words, capillary storage 16 receives excess flowable substance and prevents uncontrolled leakage of the flowable substance from the outlet 15, or other portions of the implement. The excess flowable substance in capillary storage 16 will return to the reservoir 11 through channel 14 when the pressure in the reservoir 11 subsides. This process is repeated whenever temperature fluctuations, for example, cause air volume fluctuations within the reservoir 11. As the flowable substance stored in capillary storage 16 is always returned to reservoir 11, the capillary storage will not already be filled to capacity when there is an air expansion. Also, even though channel 14 is continuously wetted with flowable substance, at least in the area of opening 12, air cannot interrupt the return of the flowable substance 13 to the reservoir 11 as long as there is flowable substance in the capillaries of the storage 16 which are larger than the largest pore in the channel 14.

Figure 3:
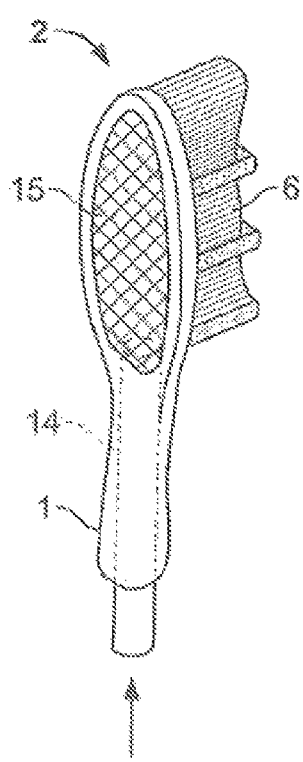
FIG. 3 is a rear perspective view of the head of the toothbrush shown in FIG. 1.
Figure 4:
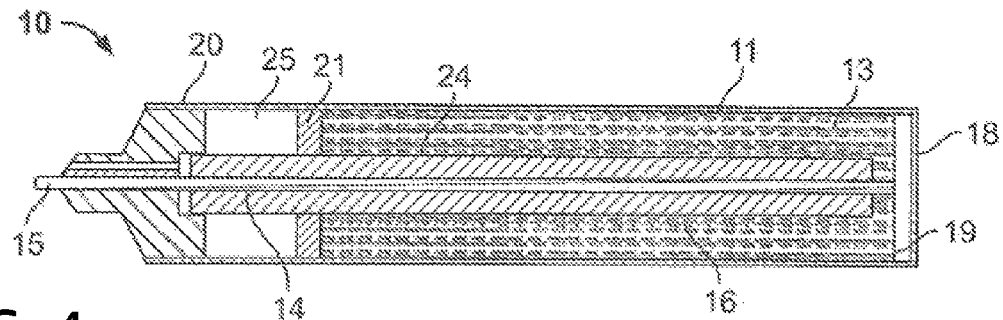
FIGS. 4-7 show examples of capillary configurations that can be used with the oral care implement.
Figure 6:
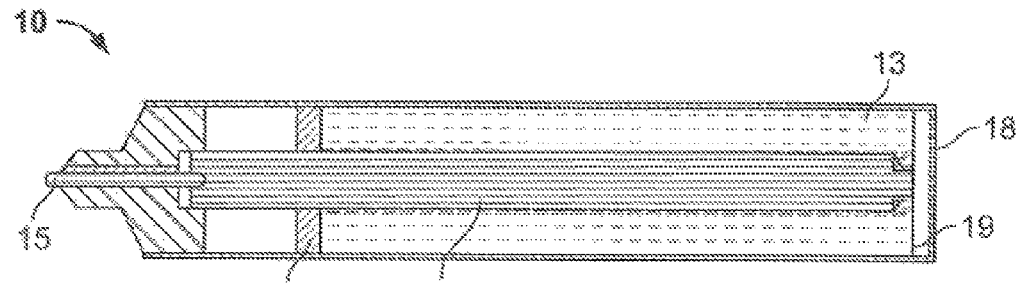
Figure 7:
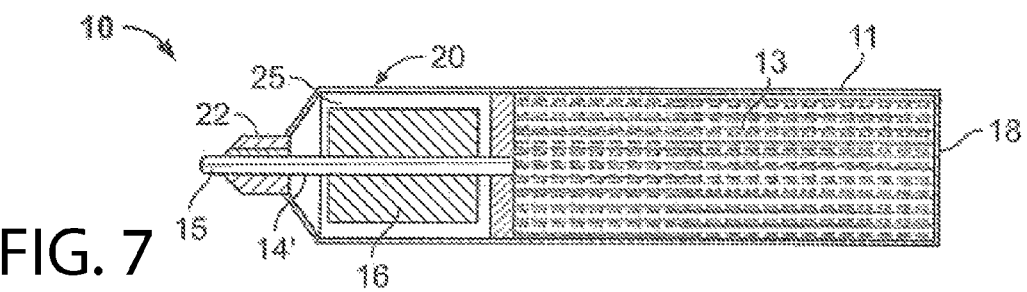

Although the outlet 15 is illustrated in FIGS. 1, 3, 5, and 6 as a separate element from the channel 14, it should be recognized that the outlet 15 may alternatively be integral with the channel 14, as schematically shown in FIGS. 4 and 7. When the outlet 15 is formed from a porous material, its pores generally should be smaller than those of the channel 14 to ensure that the flowable substance in the channel 14 will flow toward the outlet 15 during dispensing. With reference to FIGS. 4 and 6, channel 14 may be configured so that it extends into area 19 near the reservoir base 18. In this type of configuration, the capillary storage and the capillary channel 14 usually are enclosed by a tube 24. The tube 24 provides additional protection against unwanted leakage.

In the configuration shown in FIG. 4, capillary storage 16 and capillary channel 14 are separate structural elements and the channel 14 extends into base area 19. In the configuration shown in FIG. 6, a mixture of porous materials having the requisite combination of capillary sizes form a unitary capillary storage 16 and channel 14.

In the configuration shown in FIG. 5, channel 14 and capillary storage 16 define a unitary structural element similar to that shown in FIG. 6. The rear portion 140 of the integral channel and capillary storage is tapered so that it may be received in opening 12. To ensure that there is a sufficient amount of fine, flowable substance transferring capillaries in the opening 12, this portion of the combined channel/storage may be pinched together at the opening in a defined manner. The rear portion 140 may also be provided as a separate element that is connected to the capillary storage.

As shown, for example, in FIG. 7, capillary channel 14' may be configured so that it includes a radially extending portion that separates the reservoir 11 from the overflow chamber 25. The channel 14' and radially extending portion fill the opening between the reservoir 11 and the overflow chamber 25. The pores in the radially extending portion may be substantially similar to those in the channel 14' and allow air to pass, but block the flow of flowable substance. As a result, the radially extending portion may be used to regulate the flow of air into the channel 14'.

Examples of capillary flow systems of this general type are shown, for example, in U.S. Pat. Nos. 5,102,251; 5,352,052; 6,089,776; 6,095,707; 6,164,858; 6,183,155; 6,322,268; and 6,497,527, the disclosures of which are hereby incorporated by reference.

In another aspect, a vibratory device can be provided to vibrate the toothbrush or a portion thereof, such as the head 2 or a portion thereof. The vibration-producing device can be used to vibrate tooth cleaning elements 6 and 7 and/or soft tissue cleaning elements while, at the same time, promote delivery of the flowable substance(s) through the capillary channel 14 to provide an enhanced cleaning action.

A wide variety of vibratory devices can be used to produce vibrations over a wide range of frequencies to meet the needs of a particular application. Various types of vibratory devices are commercially available, such as transducers. One example of a vibratory device provides frequencies in the range of about 100 to 350 kHz. The vibration frequencies may be of different waveforms, including sinusoid, square, sawtooth and the like. Nevertheless, other values and waveforms are possible. A vibratory device may be located in head of the toothbrush or neck thereof. When activated, vibratory device is powered by battery (and controlled by electronics on circuit board or switching system) so as to induce vibrations in head of the toothbrush and thereby enhances teeth-cleaning action imparted by the tooth cleaning elements. In alternate embodiments, a vibratory device may include a micro motor attached to a shaft, with the shaft coupled to an eccentric rotating about an axis parallel to the longitudinal axis of the toothbrush. In still other embodiments, a vibratory-producing device includes an eccentric that is driven by a micro motor in a translatory manner.

A switch, such as a button, toggle switch, rotating dial, or the like, can be provided for activating the vibratory device. A vibratory device often has a power source, such as a battery. Activating the switch can cause the vibration-producing device to operate for a user-defined interval (e.g., during the time that a button is depressed or a switch is in an engaged position), or alternatively can activate a timing circuit that causes the vibratory device to operate for a predetermined interval. If a timing circuit is used, the associated interval either may be preset or may be adjustable, e.g., by a user-activated rotating dial.

Additional embodiments of the invention include configurations of vibratory device(s), bristles (or other tooth cleaning elements) and other components as described in U.S. patent application Ser. No. 10/768,363 (filed Jan. 30, 2004 and titled "Toothbrush with Enhanced Cleaning Effects"), published as U.S. Pat. Pub. No. 20050091769A1, incorporated by reference herein. For example, the neck portion of the toothbrush can be provided with neck-part zones made of an elastically relatively compliant material so as to increase the elasticity of the neck part. This would permit the head, during use of the toothbrush, to be forced back resiliently in the case of forces acting in the direction of the brushing surface. Optionally, the neck-part zones could be designed as notches which extend over part of the neck circumference and are filled with elastically compliant material (e.g. with thermoplastic elastomer).

The outlet 15 can be incorporated into an elastomeric material to provide a tissue cleanser, which can be used, for example, for cleaning the tongue, cheeks, lips, and/or gums. A tissue cleaner may employ a variety of suitable biocompatible resilient materials, such as elastomeric materials. To provide optimum comfort as well as cleaning benefits, an elastomeric material usually has a hardness property in the range of A8 to A25 Shore hardness, such as styrene-ethylene/butylene-styrene block copolymer (SEBS), available from GLS Corporation.

A tissue cleanser can be configured with a multiplicity of tissue engaging elements, which can be formed as nubs. As used herein, a "nub" is generally meant to include a column-like protrusion (without limitation to the cross-sectional shape of the protrusion) which is upstanding from a base surface. In general, the nub can have a height that is greater than the width at the base of the nub as measured in the longest direction. Nubs also can include projections wherein the widths and heights are roughly the same or wherein the heights are somewhat smaller than the base widths.

Such tissue engaging elements can help reduce a major source of bad breath and improve hygiene. Nubs enable removal of microflora and other debris from the tongue and other soft tissue surfaces within the mouth. The tongue, in particular, is prone to develop bacterial coatings that are known to harbor organisms and debris that can contribute to bad breath. This microflora can be found in the recesses between the papillae on most of the tongue's upper surface as well as along other soft tissue surfaces in the mouth. When engaged or otherwise pulled against a tongue surface, for example, the nubs of elastomeric tissue cleanser can provide for gentle engagement with the soft tissue while reaching downward into the recesses of adjacent papillae of the tongue. The elastomeric construction of a tissue cleanser also enables the base surface to follow the natural contours of the oral tissue surfaces, such as the tongue, cheeks, lips, and gums of a user. In addition, the soft nubs are able to flex as needed to traverse and clean the soft tissue surfaces in the mouth along which it is moved.

The nubs often are conically shaped, such as in the shape of a true cone, frusto-conically shaped elements, and other shapes that taper to a narrow end and thereby resemble a cone irrespective of whether they are uniform, continuous in their taper, or have rounded cross-sections. The smaller width or diameter of the tip portion in conjunction with the length of the conically shaped nub enable the nubs to sweep into the recesses of the tongue and other surfaces to clean the microbial deposits and other debris from the soft tissue surfaces. The nubs also are able to flex and bend from their respective vertical axes as lateral pressure is applied during use. This flexing enhances the comfort and cleaning of the soft tissue surfaces. Alternatively, tissue cleaning elements may have other shapes. As one example, the tissue cleanser may have different forms, including grated forms, such as described in co-pending U.S. patent application Ser. No. 11/566,479, filed Dec. 4, 2006, which is incorporated herein by reference.

The medium containing the flowable substance can be incorporated into a sealed reservoir 11 during manufacture of the toothbrush, in which case the toothbrush can be disposed of after the supply of the flowable substance is exhausted. Alternatively, the reservoir 11 can be refillable through an inlet (not shown), and/or can be replaceable, e.g., by inserting a replaceable cartridge into a recess in the toothbrush. The cartridge can be spring-loaded to stay in place after insertion, and can have a seal to prevent unwanted leakage of the flowable substance.

As illustrated in FIG. 1, the toothbrush can comprise a brush section A and a reservoir section B that are joined to each other, e.g., by threaded engagement, snap-fitting, or the like. The reservoir section B can be disposable, refillable, and/or interchangeable with other reservoir sections B containing different flowable substances, for example.

Optionally, a user-activated switch, such as a dial (not shown), can have multiple settings for selecting one or more of several flowable substances. For example, the dial can have a first setting for oxidizer/whitener treatment, a second setting for breath freshener treatment, and a third setting for antimicrobial treatment. The toothbrush can be supplied in the form of a kit including a toothbrush or a brush section A thereof, and one or more cartridges or reservoir sections B containing flowable substance(s). Multiple cartridges can be provided, for example, for supplying different flowable substances or a replacement supply of the same flowable substance.

In FIG. 1, a toothbrush is shown schematically having a head 2, bristles 6, and a handle 1. It should be understood that any bristle configuration and any handle configuration can be used, and the present invention should not be regarded as being limited to any particular configuration.

The toothbrush can be used by brushing the teeth or gums using bristles 6 and/or other tooth cleaning elements and/or by massaging the tongue, gums, or other regions of the oral cavity with a tissue cleanser. The flowable substance can be administered through one or more outlets present in or near the tooth cleaning elements and/or within the tissue cleanser and/or on other locations on the toothbrush. Depending on the type of flowable substance used and the location of the outlet (s), the flowable substance can be administered before, during, or after brushing.

Non-limiting examples of flowable substances which can be used include antibacterial agents, whitening agents, anti-sensitivity agents, anti-inflammatory agents, anti-attachment agents, plaque indicator agents, flavorants, sensates, and colorants. Examples of these agents include metal ion agents (e.g., stannous ion agents, copper ion agents, zinc ion agents, silver ion agents) triclosan; triclosan monophosphate, chlorhexidine, alexidine, hexetidine, sanguinarine, benzalkonium chloride, salicylanilide, domiphen bromide, cetylpyridinium chloride, tetradecylpyridinium chloride, N-tetradecyl-4-ethylpyridinium chloride (TDEPC), octenidine, delmopinol, octapinol, nisin, essential oils, furanones, bacteriocins, flavans, flavinoids, folic acids, vitamins, hydrogen peroxide, urea peroxide, sodium percarbonate, PVP-$H_2O_2$, polymer-bound perxoxides, potassium nitrates, occluding agents, bioactive glass, arginine salts, arginine bicarbonate, bacalin, polyphenols, ethyl pyruvate, guanidinoethyl disulfide, tartar control agents, anti-stain ingredients, phosphate salts, polyvinylphosphonic acid, PVM/MA copolymers; enzymes, glucose oxidase, papain, ficin, ethyl lauroyl arginate, menthol, carvone, and anethole, various flavoring aldehydes, esters, and alcohols, magnolia bark extract, spearmint oils, peppermint oil, wintergreen oil, sassafras oil, clove oil, sage oil, eucalyptus oil, marjoram oil, cinnamon oil, lemon oil, lime oil, grapefruit oil, and/or orange oil.

The flowable substance can be selected to complement a toothpaste formula, such as by coordinating flavors, colors, aesthetics, or active ingredients. A flavor can be administered to create a gradual flavor change during brushing, which presently is not possible using toothpaste alone.

The flowable substance may be compatible with toothpaste, or may be unstable and/or reactive with typical toothpaste ingredients. The flowable substance also may be a tooth cleaning agent to boost the overall efficacy of brushing.

The flowable substance can be a carrier vehicle containing an oral care agent, the carrier vehicle can be in the form of an aqueous solution or in the form of gel or paste. Non-limiting examples of carrier vehicles include water, monohydric alcohols such as ethanol, poly(ethylene oxides) such as polyethylene glycols such as PEG 2M, 5M, 7M, 14M, 23M, 45M, and 90M available from Union Carbide, carboxymethylene polymers such as Carbopol® 934 and 974 available from B.F. Goodrich, and combinations thereof. The selection of a suitable vehicle will be apparent to persons skilled in the art depending on such factors as the properties of the flowable substance and the desired properties of the medium, such as viscosity. Examples of tooth whitening compositions are described in U.S. Pat. Nos. 6,770,266 and 6,669,930, the disclosures of which are hereby incorporated by reference.

The reservoir 11 can contain a quantity of the flowable substance intended for a single use or a small number of uses, or may facilitate repeated use over an extended period of time, e.g., up to several months or several years. The size of the reservoir 11 can be selected to be compatible with the desired overall dimensions of the toothbrush as well as such factors as the stability of the flowable substance and the quantity of medium administered during each application.

The supply of flowable substance in the reservoir 11 generally is free or substantially free of components which are incompatible with the flowable substance and/or the medium containing the flowable substance, such as incompatible toothpaste components as previously identified.

The toothbrush optionally can be provided with compartments and/or access panels for access to the various components, such as the power source and reservoir. The power source can be, for example, a replaceable or rechargeable battery as well known.

FIGS. 8-13 illustrate an oral care implement, such as a toothbrush 100, having a handle 103 and a head 105 which may be used for cleaning the teeth and soft tissue in the mouth, such as the tongue, interior surfaces of the cheeks, lips or the gums. Handle 103 is provided for the user to readily grip and manipulate the toothbrush, and may be formed of many different shapes and constructions. While the head is normally widened relative to the neck of the handle, it could in some constructions simply be a continuous extension or narrowing of the handle. The head 105 can have a first face 106 that supports tooth cleaning elements 107 (FIGS. 12 and 13) and a second face 108 that supports a tissue cleanser 300 (FIGS. 9 and 10), which can have one or more outlets for dispensing flowable substance(s) as previously described. The first and second faces 106, 108 can be disposed on opposite sides of head 105. Nevertheless, tissue cleanser 300 may be mounted elsewhere, such as the proximal end 104 of handle 103. The tissue cleanser 300 or portions of it may also be located on the peripheral sidewall surface 101 of head 105 or extend farther towards the proximate end 104 of handle 103 than illustrated.

Tissue cleanser 300 can be configured with a multiplicity of tissue engaging elements 303 (FIGS. 8-12), which can be formed as nubs.

Figure 9:
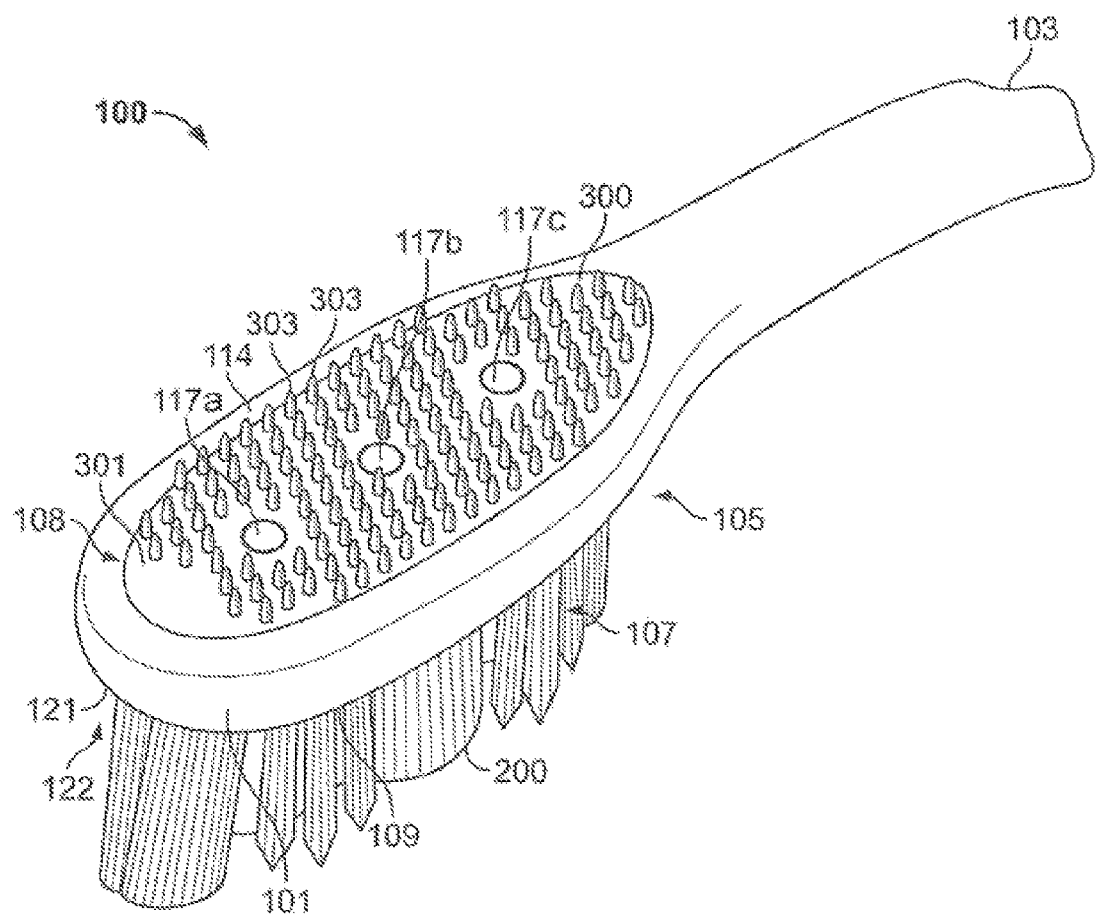
FIG. 9 is an enlarged perspective view of a head of an oral care implement of FIG. 8.
Figure 11:
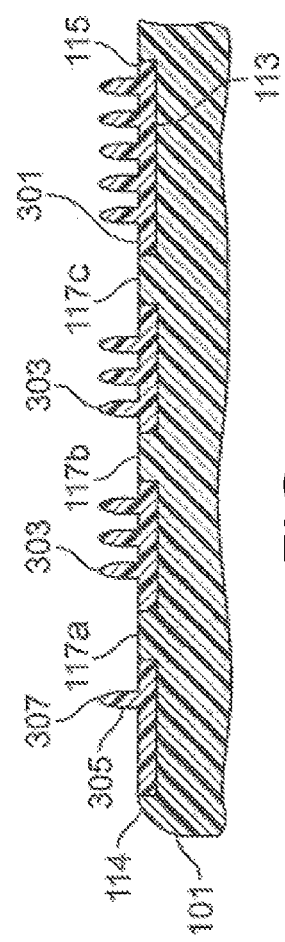
FIG. 11 is a partial section view of a head of the oral care implement of FIG. 8 taken along line 4-4 of FIG. 10.

As seen in FIGS. 9 and 11, the nubs 303 can be conically shaped. With reference to FIG. 11, the base portion 305 of each conically shaped tissue engaging element 303 can be larger than the corresponding tip portion 307. In this conically shaped configuration, the base portion 305 has a wider cross-sectional area to provide effective shear strength to withstand the lateral movement of the tissue cleanser 300 along the surface of the tongue or other soft tissue surface.

Figure 10:
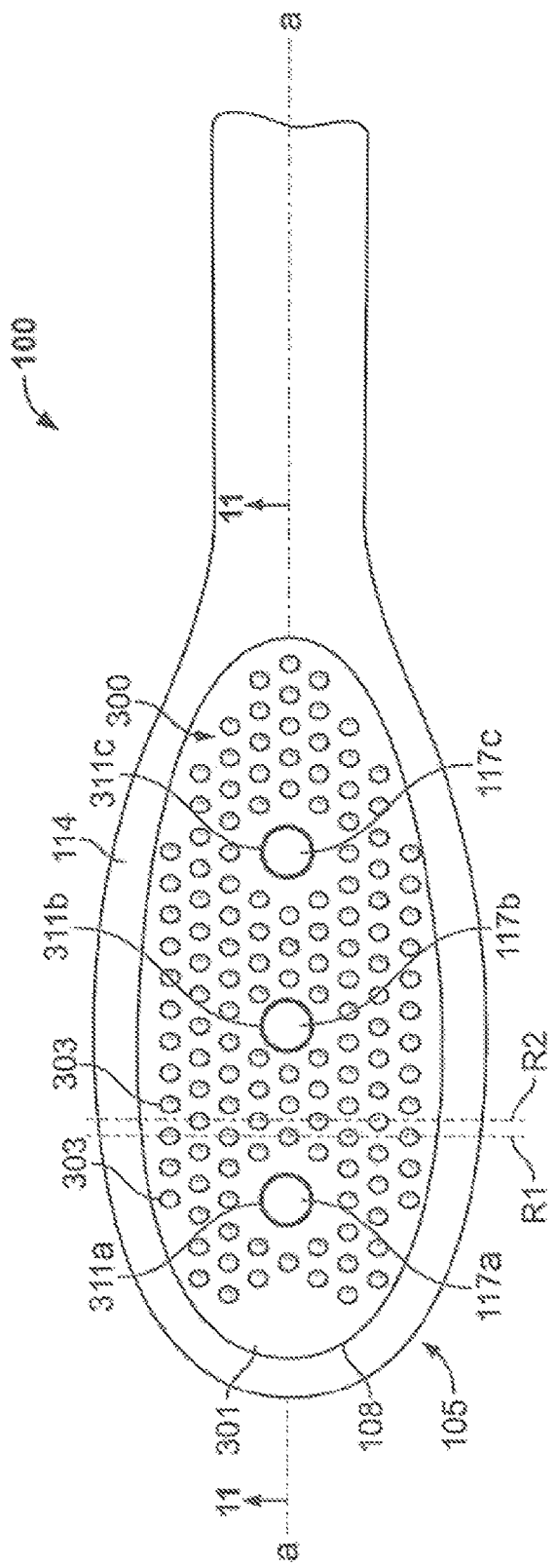
FIG. 10 is a plan view of the oral care implement of FIG. 8 illustrating a tongue cleaning feature.

As seen in FIG. 10, nubs 303 can be disposed in longitudinal rows in a direction generally parallel to the longitudinal axis a-a. Further, nubs 303 are disposed in transverse rows R1, R2 on an axis parallel to base surface 301 and generally perpendicular to the longitudinal axis a-a. Adjacent nubs 303 can be provided on the base surface 301 in a staggered arrangement. For example, adjacent transverse rows of nubs R1 and R2 can have nubs 303 that are not directly behind each other. A first nub is said herein to be "directly behind" second nub when it is located within the lateral bounds of the second nub extending in a longitudinal direction. This configuration enables improved cleaning of the soft tissue surfaces by facilitating the removal of microflora and other debris, and especially from the recesses of adjacent papillae of the tongue. Nonetheless, the nubs could be arranged randomly or in a myriad of different patterns.

Figure 8:
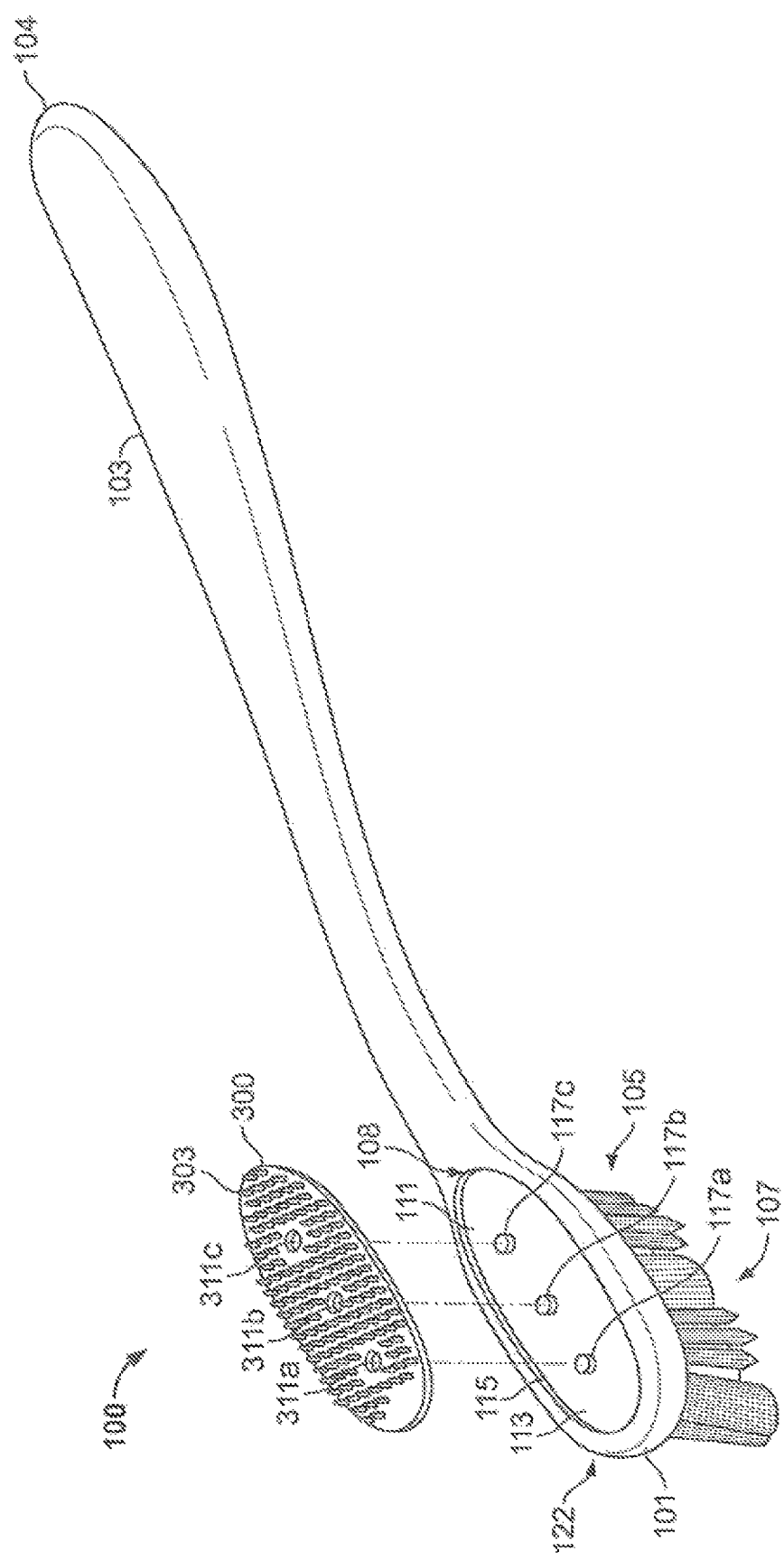
FIG. 8 is an exploded assembly perspective view of an oral care implement according to one or more aspects of an illustrative embodiment.

Tongue cleanser 300 can be formed by being molded to head 105, although other manufacturing processes could be used. With reference to FIGS. 8 and 11, tissue cleanser 300 can be molded within a basin or a receiving cavity 111 in face 108 of head 105. The receiving cavity 111 has a lower base surface 113 and a peripheral sidewall 115 extending away from the lower base surface 113. In one mounting arrangement, nubs 303 of the tissue cleanser 300 are exposed for use with the base surface of the tissue cleanser 300 being flush or recessed relative to the surface 114 of the head. Nevertheless, other orientations are possible. Also, base surface 301 of the tissue cleanser could be embedded in head 105 or covered by another layer with nubs 303 projecting through appropriate openings.

As can be seen in FIGS. 8 and 11, face 108 also can include one or more peg members 117a-c disposed within basin 111. Peg members 117 form anchor points against the opposing mold to prevent the head from moving under the pressure of the injection molding. As a result, tissue cleanser 300 can include one or more complementary apertures 311a-c which exposes the tops of peg members 117a-c. Although, the pegs are illustrated in alignment along the centerline of the head (e.g. longitudinal axis a-a), the pegs could have many different positions. Further, the pegs and basin can both be included with head 105, but either could be used without the other.

Alternatively, basin 111 and peg members 117a-c may be provided to position and hold a previously molded tissue cleanser, although these constructions are not necessary to use such a previously molded tissue cleanser.

Peg members 117a-c may take on a variety of shapes and lengths. With continued reference to the FIGS. 8 and 11, head 105 includes peg members 117a-c extending away from the lower base surface 113 of basin 111 to the height of the peripheral sidewall 115. The peg members 117a-c are shaped in the form of a cylinder, but other shapes and lengths of the peg members 117a-c are possible. While the molding process can be used to bond the tissue cleanser to the head, the tissue cleanser could be preformed and attached by adhesive or other known means.

As shown in FIGS. 8-11, tissue cleanser 300 can be formed as a pad composed of a soft and pliable elastomeric material for comfortable cleaning and effective removal of bacteria and debris disposed on the surface of the tongue, other soft tissue in the mouth and even along the lips, as well as for dispensing the flowable substance(s) as previously described. The tissue cleanser 300 also can provide effective massaging, stimulation and removal of bacteria, debris and epithelial cells from the surfaces of the tongue, cheeks, gums or lips.

Figure 12:
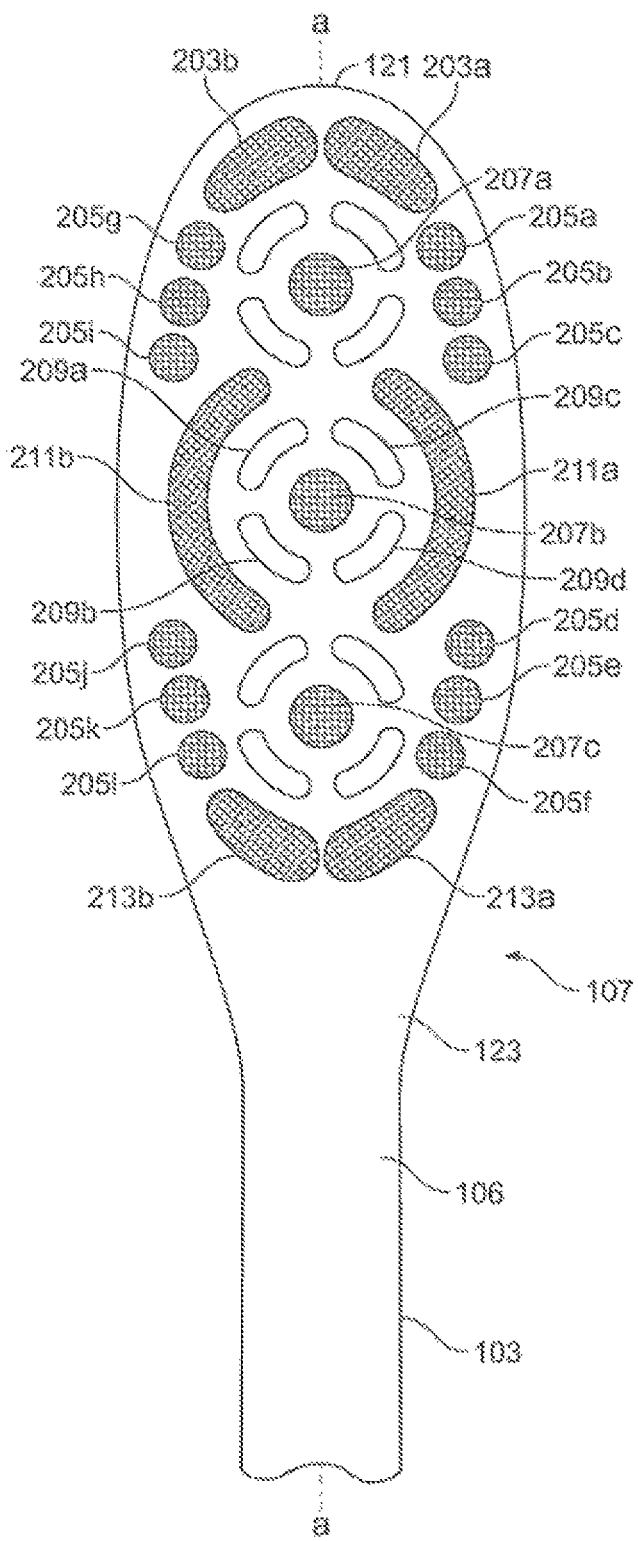
FIG. 12 is a plan view of the oral care implement of FIG. 8 illustrating at least one tooth cleaning configuration.
Figure 13:
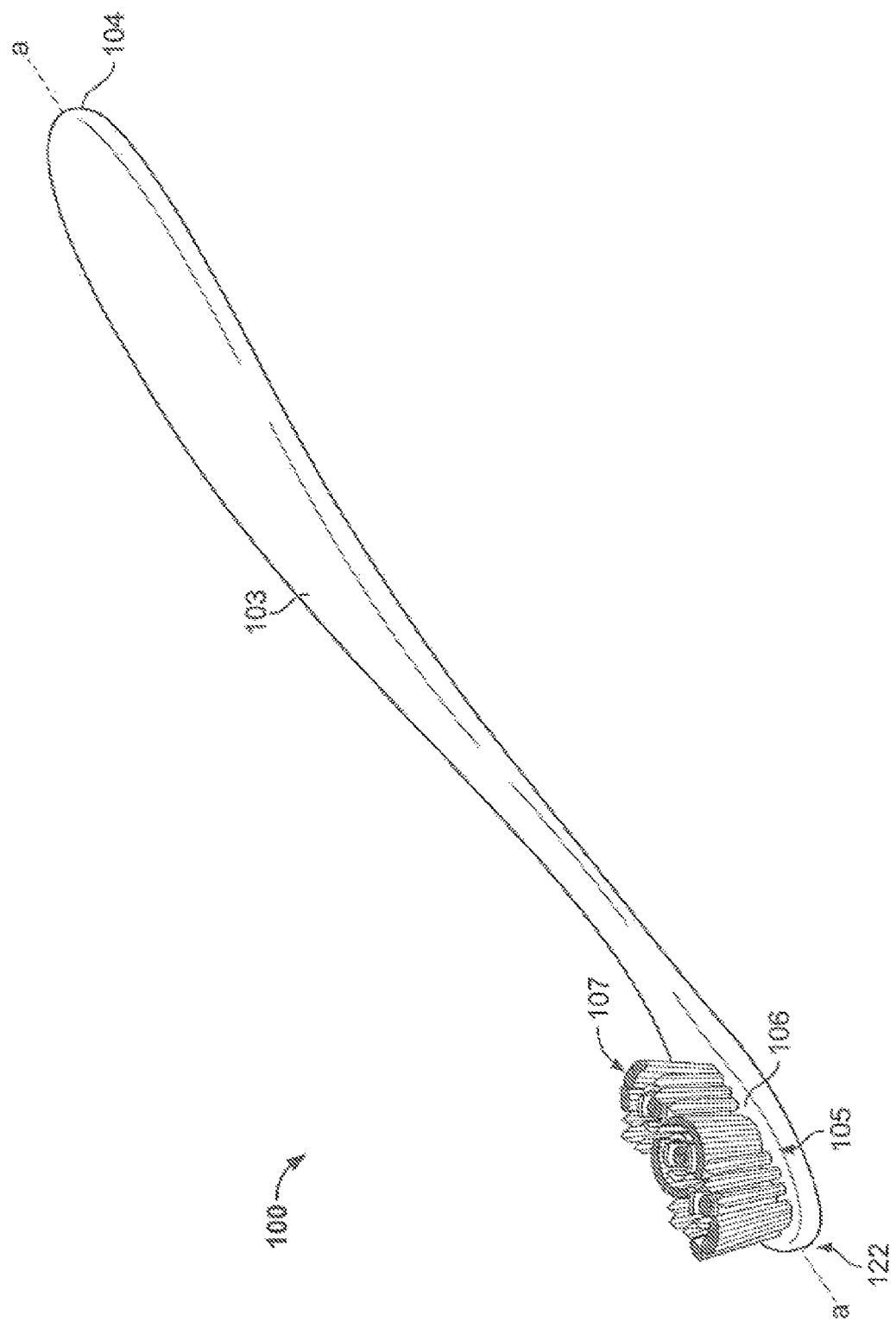
FIG. 13 is a perspective of the view of the oral care implement illustrating example tooth cleaning elements.

Referring to FIGS. 12 and 13, the tooth cleaning elements 107 of head 105 may include a variety of tooth cleaning elements which can be used for wiping, cleaning and massaging the user's teeth and gums. Any suitable form of tooth cleaning elements may be used. The term "tooth cleaning elements" is used in a generic sense which refers to filament bristles or elastomeric fingers or walls that have any desirable shape. In the illustrated example of FIG. 12, tooth cleaning elements 107 include distal tooth cleaning elements 203a-b disposed at a distal tip 121 of head 105, peripheral tooth cleaning elements 205a-l, longitudinal tooth cleaning elements 207a-c disposed along longitudinal axis a-a, arcuate tooth cleaning elements 209a-d and 211a-b, and proximal cleaning elements 213a,b. Tooth cleaning elements 205, 207, 211 and 213 can be provided as tufts of bristles whereas tooth cleaning elements 209 can be formed as elastomeric walls. Nevertheless, other forms and types of tooth cleaning elements may be used.

Figure 17:
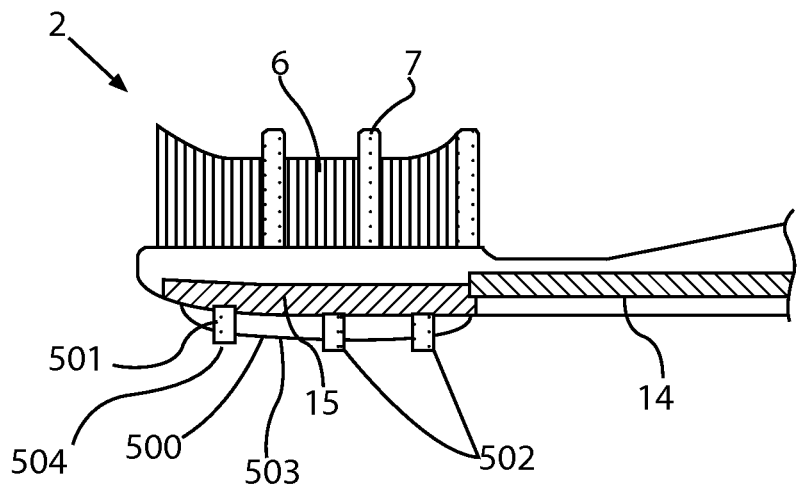
FIG. 17 is an enlarged side cross sectional view of a second embodiment of a toothbrush head including a capillary delivery system incorporated into a tissue cleanser.
Figure 18:
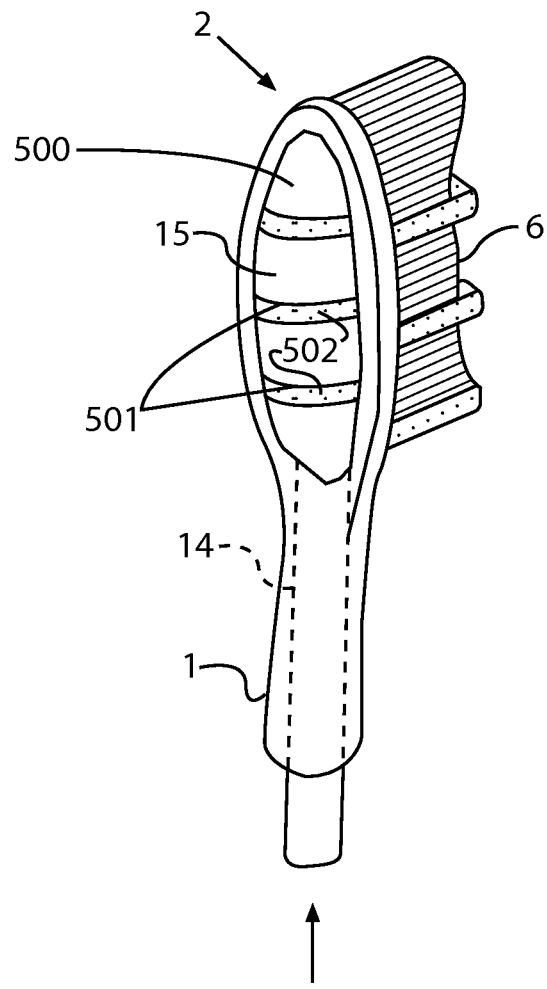
FIG. 18 is a rear perspective view thereof.

According to other embodiments, the wicking system outlet 15 may be integrated into a tissue cleanser such as the tissue cleanser 300 shown in FIG. 8-11. In lieu of the embodiment shown in FIGS. 1 and 3 wherein the capillary outlet 15 alone may be disposed on the opposite side of toothbrush head 2 from the tooth cleaning elements, the tissue cleanser may be exposed and/or extend through various shaped apertures in the tissue cleanser to dispense the flowable substance from the toothbrush to the oral cavity of the user. FIGS. 17 and 18 show one possible exemplary embodiment of such a tissue cleanser incorporating one or more capillary outlets 15.

Figure 2:
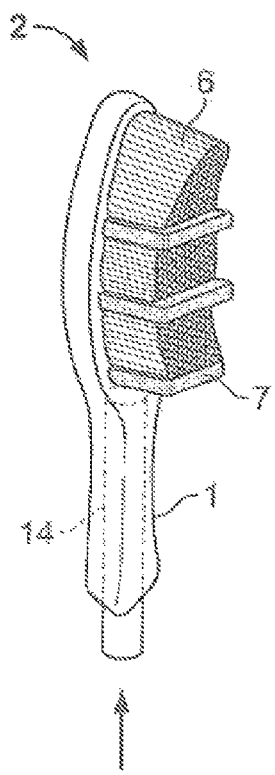
FIG. 2 is a front perspective view of the head of the toothbrush shown in FIG. 1.

FIG. 17 shows an enlarged side cross sectional view of a toothbrush head 2 configured similarly to toothbrush head shown in FIGS. 1-3. FIG. 18 is a rear perspective view of the toothbrush head shown in FIG. 17.

Referring now to FIGS. 17 and 18, head 2 of toothbrush 1 includes a tissue cleanser 500 which may be disposed on a side of the head opposite the tooth cleaning elements such as bristles 6 and/or elastomeric elements 7 as shown in one possible embodiment. Tissue cleanser 500 may generally similar to tissue cleanser 300 and include a plurality of nubs 303 similarly to those shown in FIGS. 8-11 (but omitted for clarity in FIGS. 17 and 18) and/or other projecting tissue cleansing projections or textured surfaces. Capillary outlet 15 is disposed beneath at least a portion of tissue cleanser 500 in a preferred embodiment. At least one, and preferably a plurality of apertures 501 may be formed in tissue cleanser 500 through which capillary outlet extensions 502 extend outwards from outlet 15 and toothbrush head 2 in a direction generally transverse to the head and longitudinal axis of the toothbrush 1. Outlet extensions 502 are in fluid communication with capillary outlet 15 and may be made of the same or different capillary material as outlet 15. Outlet extensions 502 may be formed integrally with outlet 15 or may be structurally separate and attached to outlet 15 by any suitable means used in the art.

The free ends 504 of outlet extensions 502 may be flush with the outer exposed surface 503 of tissue cleanser 500 in some embodiments, or in other embodiments as shown extensions 502 may project outwards above surface 503 of tissue cleanser 500 to further enhance contact of the capillary outlet extensions with oral surfaces and delivery of the flowable substance via capillary action. The height of outlet extensions 502 measured from surface 503 of tissue cleanser 500 to free ends 504 of extensions 502 may be less than, equal to, or greater than any tissue cleansing projections (such as nubs 303 shown in FIG. 11) provided on tissue cleanser 500. It is contemplated that in some embodiments, outlet extensions may have varying heights and need not be all the same.

In the exemplary embodiment shown in FIGS. 17 and 18, outlet extensions 502 (and corresponding apertures 501 in tissue cleanser 500) may be shaped as laterally extending rectangular strips for illustration purposes. However, outlet extensions 502 may have any suitable shape or be any combination of different shapes including but not limited to circular, oval, polygonal, or other. In addition, it will be appreciated that any number of outlet extensions 502 may be provided and outlet extensions 502 may be positioned anywhere in tissue cleanser 500. Accordingly, the invention is expressly not limited by the shape, number, or placement of outlet extensions 502.

Multi-Stage Capillary Flow Delivery System

According to another aspect of the invention, a multi-staged capillary or wicking flow delivery system is provided to regulate the dispensing flow rate of the flowable substance to the user. In some embodiments, such as those previously described herein with respect to FIGS. 4-7, controlling the relative dose and delivery of a flowable substance from an oral care implement to a user relies mainly on exposure time and the wicking speed through the capillary channel(s). Since users do not all brush or cleanse the teeth and/or oral soft tissue (i.e. tongue, gums, interior of mouth, etc.) in the same manner (e.g. lips open or closed, fast or slow brush strokes, high or low pressure between brush/tongue cleaner and teeth and/or tissue, etc.) or for the same period of time, this may produce variability in the dispensing rate and does not allow for precise dosing of the flowable substance.

Prior known capillary or wicking systems in non-oral fields have focused mainly on applications in which steady continuous flow is often desired. For example, in writing pen and highlighter marker applications, the ideal product delivery is a steady continuous flow which does not diminish during usage. In some situations, this kind of continuous flow would also be desirable for some oral care applications. However, in instances involving high frequency of brushing/cleansing activity or where highly regulated flowable substances would be delivered to the user, it may be desirable to more precisely regulate the flow of the oral care material to prevent overdose or over-application of the oral care material.

A multi-stage capillary or wicking flow delivery system now described provides a non-continuous dispensing system which interrupts the otherwise continuous capillary wicking action of the flowable substance to provide greater control over the dosing and delivery rate of the flowable substance to the user. The multi-stage capillary flowable substance delivery system further reduces or eliminates variability in agent delivery rates based on the user's brushing or cleansing habits.

Figure 14:
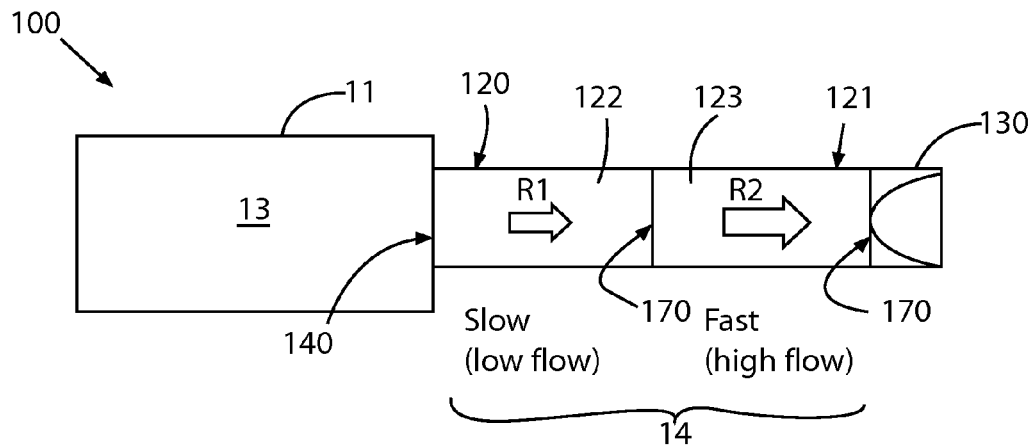
FIG. 14 is a schematic diagram of a multi-stage capillary fluid dispensing system according to one exemplary embodiment of the invention.

FIG. 14 is a schematic diagram of one exemplary embodiment of a multi-stage capillary flow dispensing system according to the present invention. The system includes a capillary device 100 having a capillary channel 14 that is in direct or indirect fluid communication with a flowable substance reservoir 11 holding a flowable substance 13. Reservoir 11 may include capillary storage such as capillary storage 16 shown in FIGS. 4-7 and described herein which is in fluid communication with capillary channel 14. Capillary channel 14 preferably is formed of a first wicking or capillary member 122 defining a flow section 120 and a second wicking or capillary member 123 defining a second flow section 121. Flow sections 120 and 121 are in fluid communication with each other and reservoir 11. In one possible embodiment, flow section 120 may be directly coupled to flow section 121 as shown. In other embodiments, intermediary flow conduits (not shown) may be provided between flow sections 120 and 121 (not shown).

Each of the wicking or capillary members 122 and 123 are structured and formed of a wicking material as further described herein so that the flowable substance flow rate or throughput through each wicking member via capillary or wicking action is different. Accordingly, in a preferred embodiment, wicking member 122 forming flow section 120 has a first flow rate R1 and wicking member 123 forming flow section 121 has a second flow rate R2 that is different than the first flow rate. In this exemplary embodiment, flow rate R1 preferably may be lower/slower than flow rate R2 (as illustrated by the flow arrows in FIG. 14).

With continuing reference FIG. 14, flow section 121 in one embodiment is preferably fabricated for fast or high rate of flow to transmit and deliver a flowable substance volume stored therein quickly in a short period of time via capillary or wicking action relative to flow section 120. In some embodiments, flow section 121 may contain a predefined dose of a flowable substance and may empty its volume completely upon activation by a user to administer the set dose.

By contrast, flow section 120, which is preferably fabricated for a slower or lower rate of flow relative to flow section 121, replenishes the flowable substance in section 121 via capillary or wicking action slowly. For example, in some representative embodiments, without limitation, it may take from several minutes to approximately 1-2 hours or more for this to occur depending on the flowable substance to be dosed to a user and dosage limitations associated with the flowable substance. Preferably, flow section 120 is fabricated so that replenishment of flowable substance in flow section 121 does not substantially occur simultaneously during usage (i.e. during emptying of section 121). Accordingly, there is preferably a lag time or replenishment period between the time in which the contents of section 121 are fully expelled and dispensed to a user and the time in which section 121 is fully replenished with a new charge of flowable substance 13. In some embodiments, this lag time may be several minutes to one or more hours. This works to deliver a maximum predefined dose of flowable substance to the user from the flowable substance charge already stored in flow section 121 prior to use and ready for delivery to the user.

In some embodiments, flow section 120 may further be fabricated to have a larger volumetric storage capacity than flow section 121 which may serve as the flowable substance dosing portion of the capillary channel 14. Since flow section 120 has a slower flow rate and therefore replenishment rate than section 121 in one embodiment, it is preferable that section 120 have a larger storage capacity than section 121 so that there is sufficient flowable substance readily available to fully recharge section 121 when its flowable substance contents are emptied upon delivering a dose to a user. Accordingly, in some embodiments, flow section 120 may have a longer axial length and/or larger transverse cross-section than section 121. It will be appreciated that capillary channel 14 and flows sections 120 and 121 may further have any suitable transverse cross-sectional shapes such as without limitation circular or segments/portions thereof, oval/elliptical or segments/portions thereof, and polygonal. Each flow section 120, 121 may further have a different transverse cross-sectional shape than the other flow section. Accordingly, the invention is not limited to any particular cross-sectional shape, dimensions, or lengths of wick or capillary channel 14 which will be dictated by the particular application and housing to be used.

In some embodiments, referring to FIG. 14, flow section 121 may be fluidly coupled to an outlet such as a conventional applicator 130 for administering the flowable substance directly to the user via surface contact with the applicator. The surface contact activates and stimulates the flow of flowable substance 111 via capillary action from reservoir 113 through capillary channel 14 and ultimately outwards from applicator 130 to the intended target delivery surface. In some embodiments, the delivery surface may be a tooth or tissue surface in the oral cavity of the user. In some embodiments, applicator 130 may be conventional nib formed of any suitable porous flowable substance-transmitting material as described herein and known to those skilled in the art. In other embodiments, flow section 121 may deliver its flowable substance contents via any other type of suitable outlet such as outlets 15 already described herein with reference to FIGS. 1-13, which in some embodiments may be incorporated into an oral care implement such as toothbrush 100 or other dispensing device. Other suitable outlets that may be used in conjunction with flow sections 102, 121 and capillary channel 14 may be incorporated into a tongue cleaner such as described herein elsewhere with respect to FIGS. 17 and 18. In yet other possible embodiments, a separate applicator or outlet structure may be omitted entirely and flow section 121 may be configured and adapted to administer the flowable substance dose directly to the user.

It will be appreciated that the foregoing exemplary multi-stage wicking construction of capillary device 100 and capillary channel 14 with flow sections 120, 121 advantageously provides the ability to deliver a predefined dose of flowable substance 13 to a user. This provides an intermittent flow mechanism and greater flow control in contrast to continuous flow type capillary and wicking systems when it is desired to regulate and administer a specific dose of a flowable substance to a user within a given treatment time period.

Wicking or capillary members 122, 123 forming fluid flow sections 120, 121 respectively may be made of any suitable wicking material having fluid capillary and wicking action properties such as those already described herein elsewhere. Accordingly, the differential flow rates R1 and R2 of flow sections 120 and 121, respectively, may be accomplished by a variety of means, including wicking material selection and/or the physical or structural design of wicking members 122, 123 using the materials and techniques already described herein with reference to FIGS. 1-13. These include, but are not limited to differences in wicking materials for constructing flow sections 120 and 121 including differing porosities (e.g. various foams or fibrous material) and/or chemical compositions (e.g. chemically-modified silica). This provides each of wicking members 122 and 123 with specific capillarities or wicking properties/characteristics to meet the desired flow rates.

The rate and amount of flowable substance 13 delivered or transferred from one flow section to another section thus may be controlled by using suitable wicking materials having different capillary properties for each flow section 120 and 121 of the multi-stage delivery system. Some exemplary suitable wicking materials may include polymers such as polyethylene, polypropylene, celluloses, wools, polyesters, collagens, nylons, and blends thereof. The polymer void volume, porosity, pore size, density, size and shape can all be tailored to provide the desired flowable substance release or flow rate characteristics from one flow section 120 to the other section 121. Additionally, the wicking materials can be treated with food grade surfactants to change their hydrophobicities and/or hydrophilicities which would also help control the rate of flowable substance release/flow and replenishment from one flow section to another.

Alternatively, as schematically illustrated in FIG. 14, flowable substance flow may be controlled between wicking members 122 and 123 by providing a flow restrictor 170 (between the wicking members such as without limitation a unidirectional or bidirectional flow gate or valve, a porous membrane, a perforated partition plate, or a diaphragm. The flows restrictors 170 regulate flow of flowable substance 13 between flow section 120 and reservoir 11, flow sections 120 and 121, and/or flow section 121 and applicator 130 (if provided). In some embodiments, the flow restrictor may be designed to open and/or permit flowable substance 13 to pass therethrough when a specific predetermined threshold pressure differential or flow has been obtained. This would have advantages such as more rapidly releasing a larger volume and reducing back-flow of liquid into the reservoir.

In some embodiments, the wicking material used for capillary channel 14 may be one continuous strip of material having differing physical and chemical properties along its core length with differing capillarities to define flow sections 120 and 121. In other embodiments, each flow section 120, 121 may be separate components and modular in design wherein each flow section of a material having differing physical and/or chemical properties and thus different capillarities can be simply joined together via any suitable means used in the art such as mechanical, adhesive, or other means. In some exemplary embodiments, flow section 121 may be plugged or snapped into section 120 and vice versa (via reduced cross-sectional extensions of either flow section) or simply press fit together with a housing or other support structure that maintains axial pressure between two opposing abutting ends of flow sections 120 and 121.

Using the foregoing principles of a multi-stage wicking or capillary system, it will be appreciated that some embodiments of capillary channel 14 may be constructed with more than two flow sections allowing the designer to customize the flow rate of flowable substance through various portions of the capillary channel and delivery of the flowable substance to the user.

Additionally, the wicking system may be designed in a concentric tubular and onion-layer like design where each "onion" layer or tube has differing flowable substance release characteristics using the materials, construction, and same design principles described herein. This embodiment of a wicking system may be configured as a combination of two or more concentric rings of wicking material (similar to those of a tree trunk). In some embodiments, the different layer rings could be extruded from different type of wicking materials that create variable wicking characteristics. The variable wicking could deliver some flowable substance quicker and then some flowable substance slower depending on the densities, material composition selected, or layer thickness. One exemplary embodiment of such a multi-layer wicking system is shown in FIG. 19.

Figure 19:
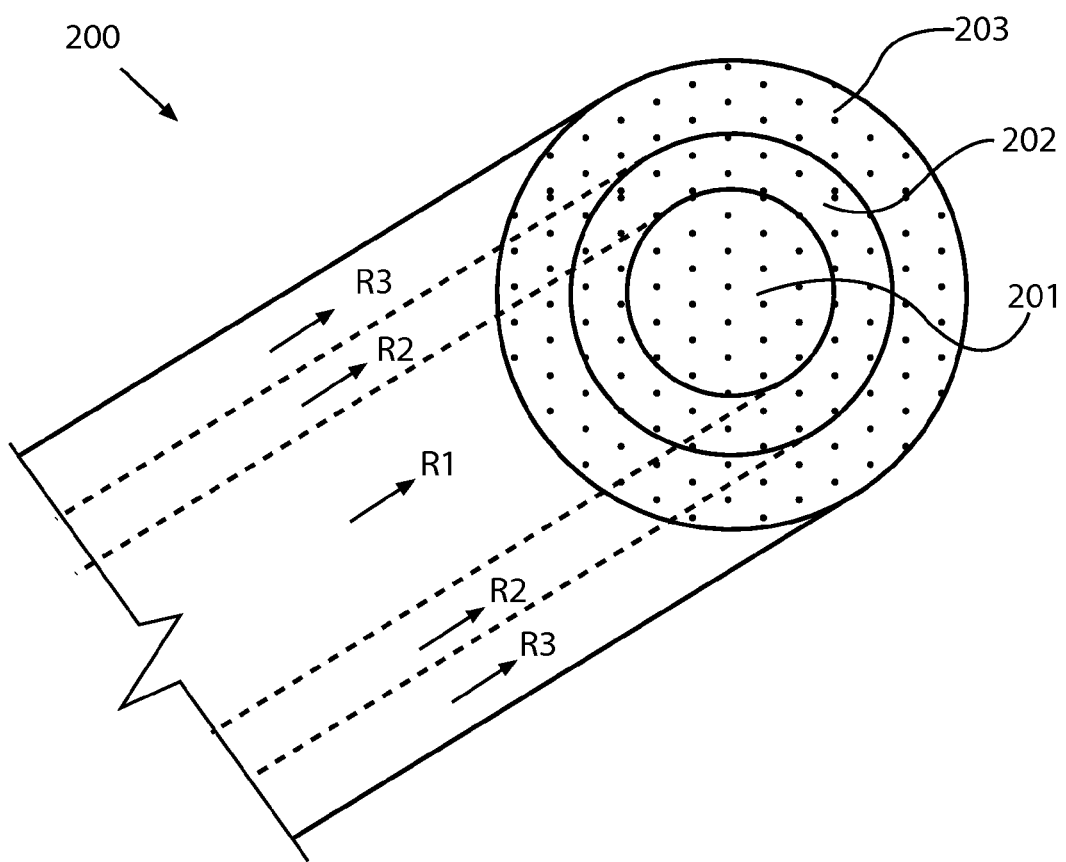
FIG. 19 is a cross-sectional perspective view of a capillary channel comprising concentrically aligned capillary or wicking members.

FIG. 19 shows a cross section of a capillary channel 200 including a combination of concentrically-aligned wicking or capillary members having different wicking characteristics or capillarities. Capillary channel 200 includes an inner-most first wicking or capillary member 201, a second wicking or capillary member 202 circumferentially disposed adjacent and in contact with member 201, and a third wicking or capillary member 203 circumferentially disposed adjacent and in contact with member 202, as shown. In one possible embodiment, capillary channel 200 may be directly or indirectly fluidly coupled to a reservoir such as reservoir 113 shown in FIGS. 14-16 or reservoir 13 shown in FIGS. 4-7. Each of the wicking or capillary members 201-203 are structured and/or formed of a wicking material as further described herein so that the fluid flow rate or throughput through each wicking member via capillary or wicking action is different. Accordingly, in a preferred embodiment, wicking member 201 has a first fluid flow rate R1, wicking member 202 has a second fluid flow rate R2, and wicking member 203 has a third fluid flow rate R3. In preferred embodiments, at least two flow rates R1-R3, and in other embodiments all three flow rates R1-R3 may be different than each other to control and establish the intended rate of flow. It will be appreciated that other embodiments may have more or less concentrically aligned wicking members.

Figure 15:
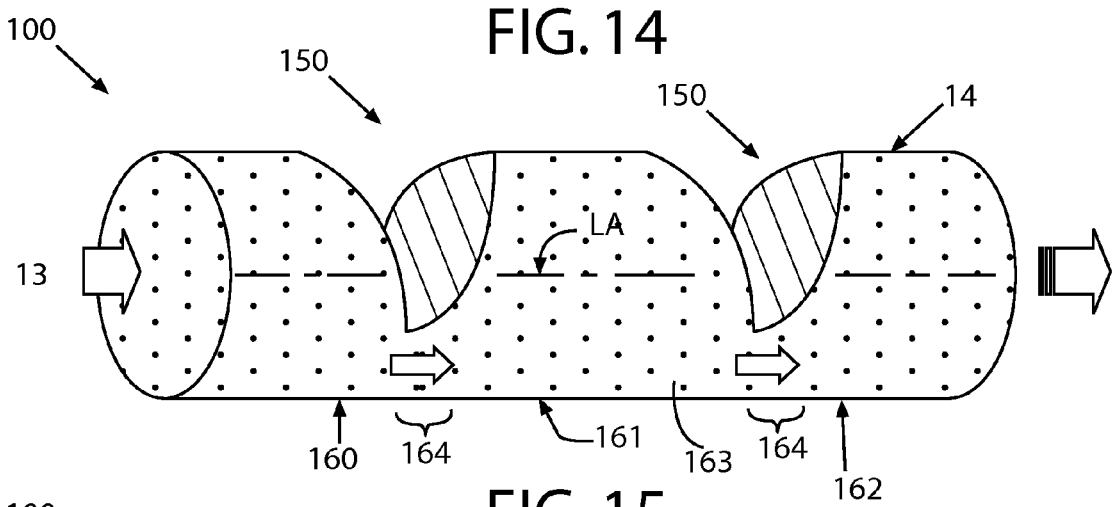
FIG. 15 is a schematic diagram of a multi-stage capillary fluid dispensing system with one embodiment of a flow restrictor.

Additional embodiments of a multi-staged capillary or wicking flow delivery system incorporating at least one flow restrictor between adjacent wicking or capillary members of capillary channel 14 will now be described. Referring to FIG. 15, a flow restrictor 150 may be formed by physically reducing the contact surface area or cross-sectional flow area between adjacent fluid flow sections of capillary channel 14, thereby inherently decreases the rate of fluid flow between each section. FIG. 15 shows one possible embodiment of a capillary channel 14 formed of a single unitary wicking or capillary member 163 defining three separate flow sections 160, 161, and 162 with flow restrictors 150 formed or disposed between each section. However, it will be appreciated that more or less flow sections and/or flow restrictors may be provided in other embodiments.

Referring to FIG. 15, flow restrictors 150 may be formed by notched portions of the capillary channel or wick. The notched portions of flow restrictors 150 extend partially through wicking member 163 in a direction generally transverse to the longitudinal axis LA of the capillary channel, thereby leaving relatively smaller connective bridges 164 between flow sections 160, 161, and 162. Flow restrictor 150 on either side of center flow section 161 reduces the flow rate between section 161 and both lateral flow sections 160 and 162 due to the reduction in cross-sectional area available to convey flowable substance 13 in relation to the rest of the wicking member 163. Accordingly, flow restrictor 150 preferably has a smaller cross-sectional flow area than adjoining flow sections 160, 161, and 162 of wicking member 163. In one possible embodiment, section 160 may be in fluid communication with a reservoir 11 holding a flowable substance 13. Flowable substance 13 is transferred through wicking member 163 via wicking or capillary action. In other embodiments, any of flow sections 160, 161 and/or 162 may be in fluid communication with fluid reservoir 11 depending on the intended design.

With continuing reference to FIG. 15, the operational principle is that the available flowable substance 13 retained in flow section 162 will be more rapidly delivered and depleted during the application process but replenished at a slower flow rate from adjoining flow section 161 due to the presence of the flow restrictor 150 between those two flow sections. Flowable substance will wick into one flow section (e.g. section 161), slow down because of the flow restrictor 150, and then wick or flow into the next downstream flow section (e.g. section 162). Accordingly, the impedance of flow through the serial arrangement shown of one or more flow restrictors and consequently each flow section downstream thereof acts to regulate the flowable substance 13 ultimately supplied to the user during application. The more upstream flow restrictors 150 such as the notches or other suitable flow restrictors that are provided in series, the longer it ultimately takes for the flow section 163 to be replenished.

Figure 16:
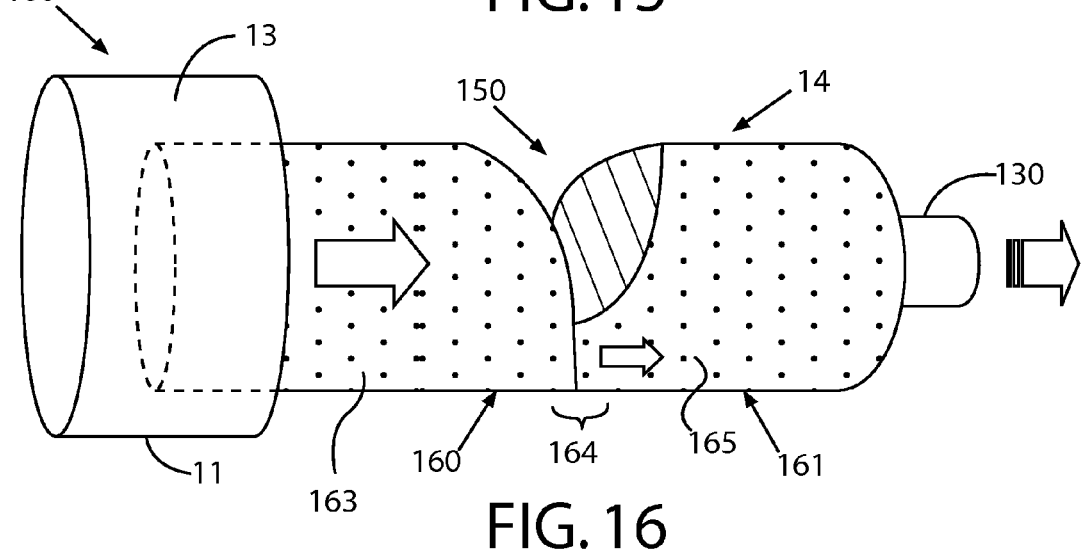
FIG. 16 is a schematic diagram of a multi-stage capillary fluid dispensing system with another embodiment of a flow restrictor.

FIG. 16 shows another embodiment of a capillary channel 14 having a flow restrictor 150 in the form of reduced contact flow surface area between flow sections 160 and 161. In this embodiment, flow sections 160 and 161 are separate unitary structures being defined by separate wicking members 163 and 165 respectively which are abutted or otherwise coupled together to form a contiguous flow path. The abutted portions of wicking members 163 and 165 defined connective bridge 164 allowing flow to pass from one flow section 160 to second flow section 161. In one embodiment, flow section 160 may be fluidly coupled to the reservoir 11 as shown. Flow section 161 may be fluidly coupled to an outlet which may be a conventional applicator 130 in some embodiments or other suitable outlet such as those described herein with respect to FIGS. 1-14.

There are a variety of other ways to form flow restrictor 150 to restrict the flow rate between different adjacent flow sections as described herein, including but not limited to: abutting at least part of an end portion of the wick or capillary member against a hard preferably nonporous surface to reduce the flow path cross-sectional area or contact area between flow sections; heat fusing or applying a non-permeable sealant to at least part of the cross-sectional end portion of the flow sections to seal at least some of the pores; cutting various other shapes or other regions from the capillary channel 14 or wick; providing more narrowly structured flow sections with smaller cross-sectional flow path cross-sectional areas between flow sections; inserting a partition wall between adjoining flow sections that has perforations or which is formed a wicking material having a lower flow throughput rate than the adjoining flow sections.

The foregoing capillary devices 100 with wicking or capillary members of capillary channels 114 shown in FIGS. 14-16 may be incorporated into any of the housings shown and described herein in FIGS. 4-7, or other suitable housings capable of supporting the wicking members. It will be appreciated that capillary devices 100 in some embodiments need not be incorporated into an oral care implement such as a toothbrush shown in FIG. 1. Accordingly, capillary devices 100 may be used in a pen-type applicator in some embodiments used for applying a flowable substance as described elsewhere herein. In yet other embodiments, capillary devices 100 may be disposed in any suitable housing used in applications completely unrelated to oral care. Accordingly, the invention is not limited to user in oral care applications alone.

It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertains, and these aspects and modifications are within the scope of the invention and described and claimed herein.

The invention claimed is:

1. A wicking device for an oral care implement having a capillary fluid dispensing system, comprising:
   a first wicking member formed of a first wicking material and defining a first flow section;
   a second wicking member formed of a second wicking material and defining a second flow section; and
   a reservoir containing a flowable substance, the reservoir being fluidly coupled to the first wicking member, the first wicking member positioned upstream of the second wicking member, and the second wicking member fluidly coupled to an outlet;
   wherein the flowable substance flows via capillary action through the first wicking member at a first flow rate and through the second wicking member to the outlet at a second flow rate, the second flow rate being greater than the first flow rate.

2. The wicking device of claim 1, wherein the outlet is an applicator for administering the flowable substance from the second wicking member to a user.

3. The wicking device of claim 2, wherein the first wicking member and the second wicking member are axially aligned along a longitudinal axis of the wicking device.

4. The wicking device of claim 1, wherein the outlet is disposed in a head of the oral care implement operative to dispense the flowable substance from the wicking device.

5. The wicking device of claim 1, wherein the first flow section is fabricated so that replenishment of the flowable substance in the second flow section from the first flow section does not substantially occur simultaneously with discharge of the flowable substance from the second flow section through the outlet.

6. The wicking device of claim 1, wherein the second flow section contains a first predefined volumetric dose of the flowable substance and dispenses the first predefined volumetric dose of the flowable substance to a user during a single use of the wicking device, and wherein the first flow section refills the second flow section with a second predefined volumetric dose of the flowable substance during a replenishment period of time that is longer than a time in which it takes to dispense the first predefined volumetric dose of the flowable substance from the second flow section so that the second predefined volumetric dose of the flowable substance is not dispensed to the user during the single use of the wicking device.

7. The wicking device of claim 1, wherein the first and second wicking materials are selected from the group consisting of polyethylene, polypropylene, celluloses, wools, polyesters, collagens, nylons, and blends thereof.

8. An oral care implement, comprising:
a handle for grasping;
a head including at least one tooth cleaning element;
a reservoir for storing a flowable substance;
at least one outlet disposed on the head; and
a wicking member fluidly coupling the reservoir to the outlet, the wicking member comprising a first flow section and a second flow section, the first flow section fluidly coupled to the reservoir and positioned upstream of the second flow section and the second flow section fluidly coupled to the outlet;
wherein the fluid flows via capillary action from the reservoir through the first flow section at a first flow rate and through the second flow section to the outlet at a second flow rate, the second flow rate being greater than the first flow rate.

9. The oral care implement of claim 8, wherein the first flow section is axially aligned with the second flow section along a longitudinal axis of the wicking member.

10. The oral care implement of claim 8, wherein the outlet is incorporated into a tongue cleaner formed in the head of the oral care implement.

11. The oral care implement of claim 10, further comprising:
at least one aperture formed into the tongue cleaner; and
at least one protuberance formed of a wicking material fluidly coupled to the outlet and extending through the aperture in a direction generally transverse to a longitudinal axis of the oral care implement.

12. An oral care implement, comprising:
a handle for grasping;
a head including at least one tooth cleaning element;
a reservoir for storing a flowable substance;
at least one outlet disposed on the head; and
a capillary channel fluidly coupling the reservoir to the outlet, the capillary channel comprising:
a first wicking member formed of a first wicking material and defining a first flow section;
a second wicking member formed of a second wicking material and defining a second flow section, the second wicking member being fluidly coupled to the first wicking member;
wherein the flowable substance flows via capillary action from the first wicking member to the second wicking member through a flow restrictor, a rate of flow of the flowable substance through the flow restrictor being different than a rate of flow of the flowable substance through the first or second wicking members.

13. The oral care implement of claim 12, wherein the outlet fluidly communicates with the second wicking member and is disposed in the head of the oral care implement for dispensing the flowable substance from the oral care implement.

14. The oral care implement of claim 13, wherein the outlet is incorporated into a tongue cleaner formed in the head of the oral care implement.

15. The oral care implement of claim 12, wherein a second flow rate of the flowable substance through the second wicking member is greater than a first flow rate of the flowable substance through the first wicking member.

16. The oral care implement of claim 12, wherein the flow restrictor comprises a reduced cross-sectional flow area disposed between the first and second wicking members that is operative to reduce the flow therebetween.

17. The oral care implement of claim 12, wherein the flow restrictor comprises a notched area formed between the first and second wicking members.

18. The oral care implement of claim 8 wherein the second flow section of the wicking member contains a predefined dose of the flowable substance, the second flow section emptying the predefined dose of the flowable material completely during a single use of the oral care implement.

19. The oral care implement of claim 18 wherein the flowable substance refills the second flow section during a replenishment period such that upon emptying the predefined dose of the flowable substance, additional amounts of the flowable substance are not applied to a user during the single use of the oral care implement.

* * * * *